United States Patent [19]

Cuzzato

[11] Patent Number: 5,345,014
[45] Date of Patent: Sep. 6, 1994

[54] PROCESS FOR PREPARING PENTAFLUOROETHANE BY DISMUTATION OF TETRAFLUOROCHLOROETHANE

[75] Inventor: Paolo Cuzzato, Treviso, Italy

[73] Assignee: Ausimont S.p.A., Milan, Italy

[21] Appl. No.: 60,222

[22] Filed: May 11, 1993

[30] Foreign Application Priority Data

May 13, 1992 [IT] Italy ............... MI 92 A 001136

[51] Int. Cl.$^5$ ............................................ C07C 19/08
[52] U.S. Cl. .................................................. 570/163
[58] Field of Search ............................ 570/163, 169

[56] References Cited

U.S. PATENT DOCUMENTS

| 2,478,932 | 8/1949 | Miller | 570/163 |
| 3,651,156 | 3/1972 | Scherer | 570/163 |
| 4,158,675 | 6/1979 | Potter | 570/169 |

FOREIGN PATENT DOCUMENTS 9219576 11/1992 World Int. Prop. O. ......... 570/169

*Primary Examiner*—Alan Siegel
*Attorney, Agent, or Firm*—Bryan Cave

[57] ABSTRACT

Pentafluoroethane (HFC 125) is selectively prepared by dismutation of tetrafluorochloroethane (HCFC 124) effected by contacting the latter, in the gas phase, with a $Cr_2O_3$ catalyst at temperatures ranging from 150° to 330° C. Along with HFC 125, also HCFC 123 substantially free from isomers 123a and 123b is obtained.

5 Claims, No Drawings

PROCESS FOR PREPARING PENTAFLUOROETHANE BY DISMUTATION OF TETRAFLUOROCHLOROETHANE

The present invention relates to a process for preparing pentafluoroethane (hereinafter referred to as HFC 125).

In particular, it relates to the preparation of pentafluoroethane by means of dismutation reaction, in the presence of catalysts, of tetrafluorochloroethane $CF_3CHClF$ (hereinafter referred to as HCFC 124).

As is known, it is useful to have available processes for the industrial production of HFC 125, which is fluorocarbon fully harmless towards atmospheric ozone and therefore an excellent potential substitute for the present CFC.

There are known processes for preparing HCFC 125 by fluorination, with HF, of proper chlorinated precursors such as HCFC 124 and 123 ($CF_3CHCl_2$). However, in order to obtain, according to such processes, appreciable conversions into the product to be obtained, severe reaction conditions are required, which generally lead to the formation of appreciable amounts of undesirable products such as, for example, CFC 114 ($CF_3CFCl_2$), which, as is known, is one of the compounds, which are harmful for ozone.

Furthermore, such processes involve the feeding of anhydrous HF at high temperature, its separation from the reaction products and the subsequent recycle or discharge, all these steps requiring corrosion-proof materials and being potential sources of both hazard and pollution.

It has now been found by the Applicant that it is possible to obtain HFC 125 with high selectivity and efficiency, without using HF, by means of a dismutation reaction of HCFC 124 in the gas phase, in the presence of a proper catalyst.

In particular, said dismutation is conducted by contacting gaseous HCFC 124 with a catalyst based on chrome oxide ($Cr_2O_3$), either as such or carried, at temperatures ranging from 150° to 330° C., preferably from 200° to 320° C. and even more preferably from 220° to 280° C. It is possible to use temperatures exceeding 330° C., however they are of little interest because they give rise to too high amounts of by-products.

The reaction is accompanied by the simultaneous formation of $CF_3CH_2Cl$ (HCFC 123) with minor amounts (less than 1%) of isomer $CF_2Cl$-$CHFCl$ (HCFC 123a) and traces of isomer $CF_2H$-$CFCl_2$ (HCFC 123b).

In consideration of the well-known usefulness of preparing HCFC 123 as much as possible free from isomers 123a and 123b, there are evident, therefore, the further advantages resulting from the preparation of HFC 125 by means of the dismutation reaction of HFC 124, as described hereinbefore.

Thus, an object of the present invention is a process for preparing HFC 125 which comprises contacting HCFC 124 in the gas phase with a $Cr_2O_3$ catalyst at temperatures ranging from 150° to 300° C.

In practice, it is operated by causing a gaseous HCFC 124 flow to pass through a catalyst bed at temperatures within said range.

Preferably, but not necessarily, it is operated with a time of contact between HCFC 124 and the catalyst, considered as the ratio between the volume of the reagent under the reaction conditions and the volume of the catalytic bed, ranging from 1 second to 20 seconds, preferably from 8 to 10 seconds.

The pressure is not critical; usually it is operated at atmospheric pressure or above the atmospheric pressure.

The HCFC 124 flow at the catalytic bed inlet can be diluted with inert gases, for example nitrogen.

The catalyst can be prepared by means of calcination, in air or in inert gas atmosphere, of chrome hydroxide, the latter being preparable according to one of the methods of the art such as, for example, precipitation with a base of a soluble chrome salt dissolved in water. The calcination temperature can range from 200° to 600° C.

As an alternative, the chrome oxide can be carried on a proper carrier having characteristics suitable for the use in fluid bed reactors, such as for example $AlF_3$.

If $AlF_3$ is utilized, this is preferably in the gamma and/or beta form, but it can contain also the delta form, generally up to 30% by weight.

The carried catalyst can be prepared according to various procedures; a preferred procedure comprises the steps of impregnating the carrier with an aqueous solution of a trivalent chrome salt, drying and then subjecting the so impregnated carrier to an activation treatment with air or nitrogen in the presence of water vapour, at temperatures from 200° to 600° C., but preferably from 350° to 500° C.

The $Cr_2O_3$ content in the carried catalyst generally ranges from 1 to 15% by weight, calculated as Cr on the catalyst.

Using $AlF_3$ as a carrier, it is preferable if it has a fluorine content corresponding to at least 90% of $AlF_3$ calculated on the total weight of the carier.

The following examples are given to illustrate, but not to limit the scope of the present invention.

EXAMPLE 1

Preparation of the Catalyst

An aqueous solution of chrome-potassium alum was treated with an ammonia aqueous solution, thereby obtaining the precipitation of chrome hydroxide in the form of a gel. This gel was washed with water, dried in air at a temperature of about 300° C., ground and kneaded again width water.

The resulting paste was extruded in the form of small cylinders of about 5 mm diameter. These were dried and calcined in air at a temperature of 550° C., so obtaining crystalline chrome oxide for about 80%.

Dismutation Reaction 300 g (250 cc) of the catalyst prepared as described above were introduced into an Inconel 600 tubular reactor having a diameter of 50 mm, equipped with a fritted bottom and electrically heated.

At 220° C. and at atmospheric pressure, 307 g/h, equal to 2.25 mols/h, of HCFC 124 were fed, thereby realizing a contact time of about 9 seconds.

The product leaving the reactor was washed in water, dried, sampled and analyzed by means of GLC, while water was titrated to determine the acidity, if any.

The reaction product had the following composition (in mols %):

| | |
|---|---|
| $CF_3$—$CF_2H$ | 14.8 |
| $C_2F_4HCl$ (mixture of isomers 124) | 70.5 |
| $CF_2Cl$—$CFHCl$ | <0.05 |

-continued

| | |
|---|---|
| $CF_3CHCl_2$ | 14.2 |
| Other products | 0.5 |

The free acidity was negligible, equal to 0.005 mols/hour.

EXAMPLE 2

It was operated under the same conditions as in example 1, except that the temperature was brought to 240° C.

The following products (mols %) were obtained:

| | |
|---|---|
| $CF_3-CF_2H$ | 18.9 |
| $C_2F_4HCl$ | 60.5 |
| $CF_2Cl-CFHCl$ | 0.1 |
| $CF_3CHCl_2$ | 19.8 |
| Other products | 0.8 |

Free acidity = 0.014 mols/hour.

EXAMPLE 3

Into the same reactor utilized in examples 1 and 2 there were fed 153 g/h, equal to 1 mol/h, of HCFC 124 diluted with 25 Nl/h of nitrogen, at a temperature of 240° C. and at atmospheric pressure.

Operating in like manner as in the preceding examples, the following products (mols %) were obtained:

| | |
|---|---|
| $CF_3-CF_2H$ | 18.9 |
| $C_2F_4HCl$ | 60.5 |
| $CF_2Cl-CFHCl$ | 0.1 |
| $CF_3CHCl_2$ | 19.9 |
| Other products | 0.7 |

Free acidity = 0.008 mols/hour.

EXAMPLE 4

Into the same reactor utilized in the preceding examples, at 320° C. and at atmospheric pressure there were fed 38 g/h (0.25 mols/h) of HCFC 124, diluted with 50 Nl/h of nitrogen.

Operating in like manner as in the preceding examples, the following products (mols %) were obtained:

| | |
|---|---|
| $CF_3-CF_2H$ | 40.9 |
| $C_2F_4HCl$ | 29.7 |
| $CF_2Cl-CFHCl$ | 0.5 |
| $CF_3CHCl_2$ | 18.6 |
| Other products | 10.3 |

Free acidity = 0.039 mols/h.

A temperature of 320° C. is therefore too high for obtaining a good selectivity of the process.

EXAMPLE 5

Preparation of carried $Cr_2O_3$

A catalyst suited to be used in a fluid bed was prepared by impregnating a granulated $AlF_3$ carrier (mixture of β, γ and/or δ phases: 25–30 mq/g, fluorine content: about 95% of the theoretical value) with an aqueous solution of $CrCl_3$, in a ratio of 492 g of $CrCl_3.6H_2O$ per kg of $AlF_3$, according to one of the methods of the art.

The catalyst so obtained was dried in oven at 20° C. for a few hours, then it was introduced into the same reactor utilized in the preceding examples, it was heated to 400° C. and treated for 10 hours with a 100 Nl/h air flow.

The chrome content of the catalyst was equal to 8% b. wg.

Dismutation Reaction 250 cc (306 g) of the catalyst so prepared were introduced into the reactor utilized in the preceding examples.

At 280° C. and at a slightly higher pressure than the atmospheric pressure, about 250 g/h of HCFC 124 were fed.

By operating in like manner as in the preceding examples, the following products were obtained (mols %):

| | |
|---|---|
| $CF_3-CF_2H$ | 11.1 |
| $C_2F_4HCl$ | 76.6 |
| $CF_2Cl-CFHCl$ | negligible |
| $CF_3CHCl_2$ | 11.5 |
| Other products | 0.8 |

0.010 moles/h of acidity were titrated in the washing water.

EXAMPLE 6 (comparative)

Into the reactor of the preceding examples there were charged 250 cc of the $AlF_3$ utilized as a carrier for the catalyst prepared in example 5, and 150 g/h (1 mol/h) of HCFC 124 were fed along with 26 l/h of $N_2$.

Operating in like manner as in the preceding examples, at 280° C. the following products (tools %) were obtained:

| | |
|---|---|
| $CF_3-CF_2H$ | 1.2 |
| $C_2F_4HCl$ | 97.4 |
| $C_2F_3HCl_2$ | 1.3 |
| Other products | 0.1 |

Therefore, the catalytic activity of the carrier only is extremely low.

EXAMPLE 7

A catalyst suitable for the use in a fluid bed was prepared as in example 5, the only exception being the final calcination, which was carried out in nitrogen instead of in air.

250 cc of the catalyst so prepared were charged into the reactor utilized in the preceding examples.

At 280° C. and at a slightly higher pressure than the atmospheric pressure, 180 g/h of HCFC 124 diluted with 25 Nl/h of nitrogen were fed.

Operating in like manner as in the preceding examples, the following products were obtained (in mols %):

| | |
|---|---|
| $CF_3-CF_2H$ | 36.7 |
| $C_2F_4HCl$ | 32.5 |
| $CF_2Cl-CFHCl$ | <0.05 |
| $CF_3CHCl_2$ | 27.8 |
| Other products | 2.8 |

Free acidity = 0.065 mols/h.

EXAMPLE 8

The reaction temperature was brought to 320° C., all the other conditions being the ones of example 5.

The following products (in mols %) were obtained:

| | |
|---|---|
| $CF_3-CF_2H$ | 17.43 |
| $C_2F_4HCl$ | 61.48 |
| $CF_2Cl-CFHCl$ | 0.10 |
| $CF_3CHCl_2$ | 15.64 |
| Other products | 5.35 |

Free acidity=0.035 mols/h.

What is claimed is:

1. A process for preparing pentafluoroethane, which consists essentially of contacting tetrafluorochloroethane in the gas phase with a catalyst consisting of chrome oxide ($Cr_2O_3$) at temperatures ranging from 150° to 330° C.

2. The process of claim 1, wherein the temperature ranges from 200° to 320° C.

3. The process of claim 1, wherein the temperature ranges from 220° to 280° C.

4. The process of claim 1, wherein the chrome oxide is in the carried form.

5. The process of claim 3, wherein the carrier consists of $AlF_3$.

* * * * *

Adverse Decision In Interference

Patent No. 5,345,014, Paolo Cuzzato, PROCESS FOR PREPARING PENTAFLUOROETHANE BY DISMUTATION OF TETRAFLUOROCHLOROETHANE, Interference No. 103,576, final judgment adverse to the patentee rendered June 7, 2000, as to claims 1-5.

*(Official Gazette September 18, 2001)*